United States Patent [19]

McIntosh

[11] Patent Number: 4,753,749
[45] Date of Patent: Jun. 28, 1988

[54] MICROBIOCIDAL CLEANING AGENT AND PREPARATION THEREOF

[75] Inventor: Robert H. McIntosh, Greensboro, N.C.

[73] Assignee: Interface Research Corporation, Atlanta, Ga.

[21] Appl. No.: 99,640

[22] Filed: Sep. 23, 1987

Related U.S. Application Data

[63] Continuation of Ser. No. 837,424, Mar. 7, 1986, abandoned, Continuation-in-part of Ser. No. 635,728, Jul. 30, 1984, abandoned, Ser. No. 658,695, Oct. 9, 1984, abandoned, Ser. No. 713,445, Mar. 19, 1985, abandoned, Ser. No. 736,652, May 21, 1985, Pat. No. 4,647,601, Ser. No. 744,916, Jun. 13, 1985, abandoned, Ser. No. 744,730, Jun. 13, 1985, abandoned, Ser. No. 744,917, Jun. 13, 1985, abandoned, Ser. No. 781,710, Oct. 2, 1985, abandoned, Ser. No. 785,069, Oct. 7, 1985, abandoned, each is a continuation-in-part of Ser. No. 570,952, Mar. 8, 1984, Pat. No. 4,608,289, which is a continuation of Ser. No. 523,734, Aug. 16, 1983, abandoned, which is a continuation of Ser. No. 226,006, Jan. 19, 1981, abandoned, which is a continuation of Ser. No. 930,879, Aug. 4, 1978, abandoned.

[51] Int. Cl.$^4$ .............................................. C11D 3/48
[52] U.S. Cl. ...................... 252/106; 252/8.8; 252/107; 252/174.16; 252/547; 252/DIG. 7; 252/DIG. 17; 558/113; 558/114; 558/133; 558/207; 558/208
[58] Field of Search ........... 252/8.8, 106, 107, 174.16, 252/547, DIG. 7, DIG. 17; 558/113, 114, 133, 207, 208

[56] References Cited

U.S. PATENT DOCUMENTS

| | | | |
|---|---|---|---|
| 2,272,668 | 2/1942 | Hönel | 558/113 |
| 2,541,088 | 2/1951 | Nikawitz | 564/481 |
| 2,552,325 | 2/1951 | Kosolapoff | 558/208 |
| 2,676,122 | 4/1954 | McCarthy | 252/8.8 |
| 2,891,878 | 4/1955 | Chamberlain | 428/421 |
| 2,970,081 | 1/1961 | McCall | 424/78 |
| 3,247,134 | 7/1962 | Hwa et al. | 521/107 |
| 3,280,131 | 10/1966 | Wakeman et al. | 252/107 |
| 3,294,775 | 12/1966 | Wasserman | 260/100 |
| 3,308,488 | 5/1965 | Schoonman | 5/500 |
| 3,312,623 | 4/1967 | Fitch et al. | 252/106 |
| 3,364,192 | 1/1968 | Leach | 558/133 |
| 3,498,969 | 3/1970 | Lewis | 558/133 |
| 3,705,235 | 12/1972 | McIntosh et al. | 424/83 |
| 3,762,415 | 10/1973 | Morrison | 128/290 |
| 3,896,101 | 7/1975 | McIntosh et al. | 252/521 |
| 3,919,410 | 11/1975 | McIntosh et al. | 424/78 |
| 3,920,836 | 11/1975 | McIntosh et al. | 424/315 |
| 3,928,563 | 12/1975 | McIntosh et al. | 424/78 |
| 3,959,556 | 5/1976 | Morrison | 428/364 |
| 4,024,324 | 5/1977 | Sparks | 526/2 |
| 4,110,504 | 8/1978 | Hull et al. | 428/97 |
| 4,119,724 | 10/1978 | Thizy et al. | 424/45 |
| 4,152,421 | 5/1979 | Tsutsumi et al. | 424/57 |
| 4,259,078 | 3/1981 | Kleber et al. | 252/8.8 |
| 4,343,853 | 8/1982 | Morrison | 428/233 |
| 4,401,712 | 8/1983 | Morrison | 428/289 |

FOREIGN PATENT DOCUMENTS

| | | |
|---|---|---|
| 0035375 | 9/1981 | European Pat. Off. |
| 2530584 A1 | 1/1977 | Fed. Rep. of Germany |
| 3014765 A1 | 10/1981 | Fed. Rep. of Germany |
| 3039437 A1 | 5/1982 | Fed. Rep. of Germany |
| 1122664 | 11/1984 | U.S.S.R. ............... 558/114 |

OTHER PUBLICATIONS

Imaev, Zh. Obshch. Khim., vol. 31, No. 6, 1767–1770, 1961.
McCoy, "Microbiology of Cooling Water", Chemical Publishing Co., New York, pp. 94–95.
Carpet and Rug Industry, "Antimicrobials: Here to Stay or Just Another Fad?", Feb., 1984, pp. 8–14.
Carpet and Rug Industry, "Antimicrobial Activity on Carpet", Apr., 1984, pp. 22–27.

Primary Examiner—Robert Wax
Attorney, Agent, or Firm—Jones, Askew & Lunsford Kilpatrick & Cody

[57] ABSTRACT

The present invention relates to microbiocidal cleansing agent and to a microbiocidal amine alkyl phosphate additive which is incorporated therein.

The microbiocidal amine alkyl phosphate has the following general structure:

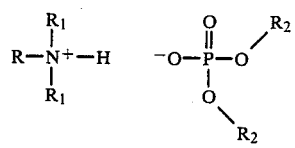

wherein
R = an alkyl group containing from 1 to 24 carbon atoms;
$R_1$ = an alkyl group containing from 1 to 3 carbon atoms; and
$R_2$ = an alkyl group containing from 1 to 5 carbon atoms.

The microbiocidal cleansing agent of the present invention may be prepared by dissolving the amine alkyl phosphate additive in water or a conventional detergent.

8 Claims, No Drawings

MICROBIOCIDAL CLEANING AGENT AND PREPARATION THEREOF

CROSS-REFERENCE TO RELATED CASES

This application is a continuation of application Ser. No. 837,424, filed Mar. 7, 1986, now abandoned, which is a continuation-in-part of Ser. No. 635,728 filed on July 30, 1984, now abandoned; application Ser. No. 658,695 filed on Oct. 9, 1984, now abandoned; application Ser. No. 713,445 filed on Mar. 19, 1985, now abandoned; application Ser. No. 736,652, filed on May 21, 1985, now U.S. Pat. No. 4,647,601; application Ser. No. 744,916 filed on June 13, 1985, now abandoned; application Ser. No. 744,730 filed on June 13, 1985, now abandoned; Ser. No. 744,917 filed on June 13, 1985, now abandoned; Ser. No. 781,710 filed on Oct. 2, 1985, now abandoned; Ser. No. 785,069 filed on Oct. 7, 1985, now abandoned; all of which are continuations-in-part of application Ser. No. 570,952 filed Mar. 8, 1984, now U.S. Pat. No. 4,608,289, which in turn is a continuation of application Ser. No. 523,734 filed Aug. 16, 1983, now abandoned, which was a continuation of application Ser. No. 226,006 filed Jan. 19, 1981, now abandoned, which was a continuation of application Ser. No. 930,879 filed Aug. 4, 1978, now abandoned.

TECHNICAL FIELD

The present invention relates to microbiocidal cleansing agents and to an additive which is incorporated therein so that the cleansing agent product is made microbiocidal. More particularly, the present invention is a cleansing agent and an additive for use therein, the combination of which may be applied to a surface for the purpose of cleaning the surface and, in addition, destroying or significantly reducing dangerous or destructive bacteria, molds and viruses that may reside on the surface to be treated.

BACKGROUND OF THE INVENTION

As used herein, the terms "antimicrobial", "bactericidal", and "fungicidal" describe the killing of, as well as the inhibition of the growth of, bacteria and fungi. The term "viricidal" is used to describe the inactivation of virus particles so that they are unable to infect host cells. The term "detergent" describes any substance or product which, when dissolved with water, is capable of dislodging, removing, and dispersing solid and liquid soils from a surface being cleansed. The term "detergent" also includes soaps comprising salts of long chain fatty acids.

A major difficulty in health care facilities, such as hospitals and nursing homes, is the spread of dangerous infectious diseases caused by a wide variety of microorganisms. The problem is exacerbated in these facilities because many of the patients are in a weakened condition due to their primary health problem. A microorganism that would not be a major threat to a healthy person could be fatal to a patient with a diminished capacity to defend himself from infection.

These potentially dangerous microorganisms are spread by a variety of vectors. One of the most common vectors is health care personnel. For example, a nurse or doctor may administer care to one patient and then be called upon to treat a second patient. Even though he or she may carefully wash his or her hands before treating the second patient, potentially dangerous microorganisms may be transferred from the first patient to the second patient. The microorganism may then cause a serious infection in the second patient.

Potentially destructive microorganisms also tend to collect and reside in clothing and in fabrics. Clothing that is used when exercising is particularly susceptible to the accumulation of potentially destructive microorganisms. If these microorganisms are not killed or inhibited, they may cause extensive damage to the fabric. Conventional detergents do not have the capability of killing many of these destructive microorganisms. A microbiocidal cleansing agent is needed that will kill or inhibit the microorganisms residing on the fabric and, at the same time, not cause any deterioration of the fabric and not cause any adverse physical reactions in the individual who is wearing the fabric.

A solution to the problem would be a cleansing agent that has the capability of killing or inhibiting a broad spectrum of microorganisms but, at the same time, is non-toxic so that the cleansing agent could safely be used around humans. Although some detergents do exhibit a certain amount of microbiocidal activity, this activity is not, in general, sufficiently high to inhibit the growth of pathogenic microorganisms. As an example, there have been epidemics in hospitals where the causative organism grew in the soap used by the health care personnel.

To increase the microbiocidal activity of detergents, microbiocidal additives can be added to detergents to improve the detergent's microbiocidal properties. Such a microbiocidal additive should have several important properties. One such property is that the additive be safe when used near or on humans and animals. Many compounds that have microbiocidal activity cannot be used in soaps and detergents because of the toxicity of these microbiocidal compounds.

The microbiocidal additive must also retain its microbiocidal activity when combined with the detergent. Many substances which, by themselves, have strong microbiocidal properties lose much, or all, of their activity when they are incorporated in detergents. For instance, chlorinated phenols exhibit a very high bacteristatic activity, but, in general, when they are incorporated in detergents, this activity is so diminished as to be of little or no value.

Thus, the control of microbial contamination is a major problem today in both industry and the home. It is difficult to develop a microbiocidal cleansing agent that is both effective in controlling the growth of a wide variety of unwanted microorganisms and is, at the same time, safe for use around human beings and animals. What is needed, both in industry and in the home, is a microbiocidal compound that can be dissolved in conventional detergents or be dissolved alone in water to provide a safe and effective microbiocidal cleansing agent.

SUMMARY OF THE INVENTION

The present invention solves the above problems by providing a non-toxic, microbiocidal cleansing agent and a water soluble microbiocidal amine alkyl phosphate additive for use therein. The water-soluble amine alkyl phosphate additive can be dissolved in water or detergent to provide a microbiocidal cleansing agent.

The detergents that can be used in the present invention include conventional detergent formulations such as linear alkyl sulfonates and alkyl benzene sulfonates. These detergents also include, but are not limited to, salts of long chain fatty acids. The microbiocidal cleansing agent of the present invention is effective in killing or significantly inhibiting the growth of a wide spectrum of both procaryotic and eucaryotic microorganisms which may reside on surfaces to be cleaned or treated with the microbiocidal cleansing agent. Thus, in accordance with the present invention, it has been determined that certain water-soluble amine alkyl phosphate additives provide unique and unexpected bactericidal properties to a conventional cleansing agent.

The amine alkyl phosphate additive can be dissolved in water at various concentrations and be used as a disinfecting agent to kill or inhibit microorganisms that may reside on that surface. For example, a solution containing from approximately 500 to 1000 parts per million (ppm) of the amine alkyl phosphate additive makes an excellent disinfectant for light duty such as mopping and cleaning of hard surfaces such as vinyl walls, floors, counters and table tops. At higher concentrations of 10% to 30% by weight in water, the amine alkyl phosphate additive performs as both a detergent and a disinfecting agent. Furthermore, the amine alkyl phosphate additive can be added to a conventional detergent at a concentration of between approximately 0.01% and 30% by weight and used to wash and disinfect fabric.

The microbiocidal cleansing agent of the present invention has the capacity to kill or inhibit the growth of many types of bacteria, fungi, viruses, yeasts and other destructive or disease-producing microorganisms which might be on a surface to be cleaned with the microbiocidal cleansing agent of the present invention.

The present invention comprises a method for the preparation of and the incorporation of amine alkyl phosphate additives into water or conventional detergents to produce microbiocidal cleansing agents. The microbiocidal cleansing agents of the present invention have the capability of killing or significantly reducing bacterial growth on surfaces cleaned with the cleansing agent.

The amine alkyl phosphate additive in accordance with the present invention is an amine alkyl phosphate having the following general formula:

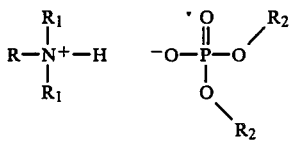

wherein
R=an alkyl group containing from 1 to 24 carbon atoms;
$R_1$=an alkyl group containing from 1 to 3 carbon atoms; and
$R_2$=an alkyl group containing from 1 to 5 carbon atoms.

The amine alkyl phosphate additive is present in the microbiocidal cleansing agent of the present invention at a concentration of between approximately 0.01% and 70% by weight.

Accordingly, it is an object of the present invention to provide a microbiocidal cleansing agent and a microbiocidal amine alkyl phosphate additive for use therein.

It is another object of the present invention to provide a amine alkyl phosphate additive which can be dissolved in water or conventional detergents to provide a microbiocidal cleansing agent with microbiocidal activity against microorganisms.

It is another object of the present invention to provide a amine alkyl phosphate additive which can be dissolved in water or added to a conventional detergent to provide a microbiocidal cleansing agent with microbiocidal activity against microorganisms.

It is still another object of the present invention to provide a microbiocidal cleansing agent that can be used to clean and sanitize clothing and other fabrics.

It is another object of the present invention to provide a microbiocidal cleansing agent which is highly effective in killing or inhibiting the growth of microbial organisms but is safe for use around humans and animals.

It is a further object of the present invention to provide a microbiocidal additive which is water-soluble and can be used in concentrated form in water to provide a microbiocidal hand soap for use where strong microbiocidal activity is required.

It is yet another object of the present invention to provide a microbiocidal additive which can be dissolved over a wide concentration range in a detergent without adversely affecting the physical properties of the detergent.

These and other objects, features and advantages of the present invention will become apparent after a review of the following detailed description of the disclosed embodiment and the appended claims.

DESCRIPTION OF THE DISCLOSED EMBODIMENT

In accordance with the present invention, the microbiocidal cleansing agent is a prepared by dissolving a microbiocidal amine alkyl phosphate in a conventional detergent or water.

An unexpected aspect of the combination of detergent or water and the amine alkyl phosphate additive is the unique ability of the additive to kill a wide variety of microorganisms including fungi, viruses and bacteria. The amine alkyl phosphate additive has been discovered to kill or inhibit the growth of the following Gram negative and Gram positive bacteria: *Sarcina lutea, Staphylococcus species, Pseudomonas aeruginosa, Pseudomonas cepecia, Escherichia coli, Escherichia communior, Bacillus subtilis, Klebsiella species, Salmonella species, Enterobacter aerogenes* and *Streptococcus species*. The amine alkyl phosphate additive also inhibits the growth of the following fungi and yeasts: *Candida albicans, Trichophyton metagrophytes, Trichophyton rubrum, Trichophyton interdigitale* and *Aspergillus niger*. In addition, the amine alkyl phosphate additive also inactivate *Herpes simplex* virus.

The amine alkyl phosphate additive in accordance with the present invention is an amine alkyl phosphate derivative having the following formula:

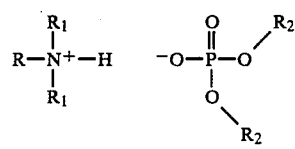

wherein
R=an alkyl group containing from 1 to 24 carbom atoms;

$R_1$ = an alkyl group containing from 1 to 3 carbon atoms; and $R_2$ = an alkyl group containing from 1 to 5 carbon atoms.

The amine alkyl phosphate additive is present in the microbiocidal cleansing agent of the present invention at a concentration of between approximately 0.01% and 70% by weight.

A preferred embodiment of the amine alkyl phosphate additive has the following formula:

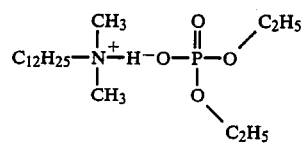

The amine alkyl phosphate additive is soluble in water. The water-soluble amine alkyl phosphate additive is a very effective surface active agent when dissolved in water. When the amine alkyl phosphate additive is dissolved in water, the resulting solution has excellent cleaning, foaming and grease extracting properties. The amine alkyl phosphate additive can therefore be dissolved in water at various concentrations and be used as a disinfectant to clean a surface as well as to kill or inhibit microorganisms that may reside on that surface. For example, a solution of the amine alkyl phosphate additive containing from approximately 500 to 1000 parts per million (ppm) of the amine alkyl phosphate additive makes an excellent microbiocidal cleansing agent for light duty such as mopping and cleaning of hard surfaces such as vinyl walls, floors, counters and table tops.

For more demanding microbiocidal activity such as that required for a surgical scrub, the preferred embodiment of the amine alkyl phosphate additive can be dissolved in water at a concentration of between approximately 15% and 70% by weight to make a heavy duty microbiocidal cleansing agent. The amine alkyl phosphate additive can also be safely used at a concentration of 100% as a hand soap. At a concentration of 100%, the amine alkyl phosphate additive is in paste form and, when used as a hand soap with water, will form a lather. Thus, the amine alkyl phosphate additive is an excellent soap as well as an unexpectedly potent water-soluble microbiocidal additive.

The preparation of the amine alkyl phosphate additive for use in the present invention involves two chemical reactions. In the first reaction, one mole of phosphorous pentoxide is reacted with three moles of a hydroxyl alkyl with from 1 to 5 carbon atoms. The mixture of reactants is heated to a temperature of between approximately 60° and 100° C. The phosphorous pentoxide is slowly added to the hydroxy alkyl while the mixture is vigorously agitated. The reaction is complete two to four hours after the addition of phosphorous pentoxide is completed.

The product formed in this reaction is a mixture of mono-ester acid phosphate and di-ester acid phosphate. The reaction equation is as follows:

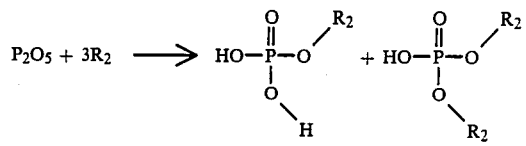

wherein $R_2$ = an alkyl group containing from 1 to 5 carbon atoms.

In the second reaction, the mixed phospho mono- and di-ester is then reacted with a tertiary amine as shown in the following reaction:

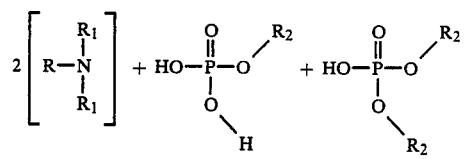

Resulting in a mixture of the following mono- and di-ester products:

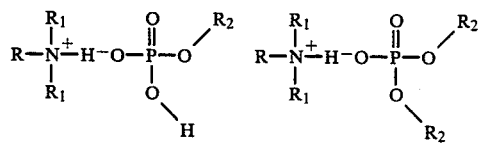

wherein

R = an alkyl group containing from 1 to 24 carbon atoms;

$R_1$ = an alkyl group containing from 1 to 3 carbon atoms; and $R_2$ = an alkyl group containing from 1 to 5 carbon atoms.

To obtain the amine alkyl phosphate, the second reaction is carried out in the following manner. Approximately 2 moles of the tertiary amine per mole of the mixed diphospho esters from the first reaction is slowly added to the mixture from the first reaction until the pH is between approximately 5 and 6 in a 75% ethanol solution. This reaction is carried out at a temperature of between approximately 80° C. and 120° C.

The preferred tertiary amine used to prepare the amine alkyl phosphate additive is dodecyl bis(methyl)-cocoamine. The preferred phosphate esters used to prepare the phosphate additive are ethyl acid phosphates. The amine alkyl phosphate additive made with the ethyl acid phosphates is soluble in ater.

The amine alkyl phosphate additive is effective when present in the microbiocidal cleansing agent of the present invention at a concentration of between approximately 0.01 to 70%. The preferred range of amine alkyl phosphate additive in the microbiocidal cleansing agent of the present invention is between approximately 0.1 and 30%. The most preferred range of amine alkyl phosphate additive in the microbiocidal cleansing agent is between approximately 0.5% and 10%.

The microbiocidal activity of the amine alkyl phosphate additive is evaluated as follows. Petri dishes are prepared using appropriate nutrient agar as a food source for the microorganism to be tested. The microorganism is evenly streaked onto the agar to form a lawn of microorganisms as is well known to one of ordinary skill in the art. 0.05 ml of each of the indicated test compounds is placed in the center of an innoculated petri dish and incubated for 24 hours at 37° C. After the 24 hour incubation period, the relative susceptibility of the test organisms to the amine alkyl phosphate additive is demonstrated by a clear zone of growth inhibition around the test solution. This zone of inhibition is the result of two processes: (1) the diffusion of the compound through the nutrient agar and (2) growth of the bacteria. As the phosphate additive diffuses through the agar medium from the drop, the concentration of the additive progressively diminishes to a point where it is no longer inhibitory for the test organism. The area of the suppressed microbial growth, the zone of inhibition, is determined by the concentration of the amine alkyl phosphate additive present in the area. Therefore, within the limitations of the test, the area of the zone of inhibition is proportional to the relative susceptibility of the microorganisms to the solution of the amine alkyl phosphate additive.

After the 24 hour incubation period, each plate is examined and the diameters of the complete inhibition zones are noted. The zones of inhibition are measured using either reflected light and sliding calipers, a ruler, or a template prepared for this purpose. The end point, measured to the nearest millimeter, should be taken as the area showing no visible growth that can be detected with the unaided eye minus the area of the test drop or sample.

The following examples will serve to further illustrate the present invention without, at the same time, however, constituting any limitation thereof.

EAMPLE I

An amine alkyl phosphate additive was prepared as follows. One mole of phosphorous pentoxide was reacted with three moles of ethanol at a preferred temperature of 80° C. The phosphorous pentoxide was slowly added to the ethanol while the mixture was vigorously agitated. At the preferred reaction temperature of 80° C. the reaction was complete in about two hours.

Next, the product of the reaction between phosphorous pentoxide and ethanol was reacted with dodecyl bis(methyl)cocoamine. 2 moles of bis(methyl)cocoamine per mole of mixed mono- and di-phospho-ethyl esters was slowly added to the mixture from the first reaction until the pH was between approximately 3.2 and 3.8 in a 75% ethanol solution. This reaction was carried out at a temperature of 100° C. The reaction mixture was vigorously agitated during the reaction.

The following two reactants were then reacted together:
(1)=2 moles dodecyl bis(methyl)cocoamine
(2)=1 mole ethyl phosphate from the above reaction
The dodecyl bis(methyl)cocoamine was slowly added to the mixed ethyl esters until the pH was between approximately 5 and 6 in a 75% ethanol solution. This reaction was carried out at a temperature of 100° C. The reaction mixture was vigorously agitated during the reaction. The resulting amine alkyl phosphate additive was used to prepare a microbiocidal cleaning agent or disinfectant.

EXAMPLE II

An aqueous solution of the microbiocidal cleansing agent of the present invention was prepared by mixing the amine alkyl phosphate additive from Example I with a solution of All ®, an aqueous detergent solution. The concentration of amine alkyl phosphate additive was 0.05% by weight. The microbiocidal detergent was heated to 85° C. Cotton fabric was then introduced and remained in the heated solution for 15 minutes. The fabric was then rinsed in water at 40°, removed and dried.

Square samples of the treated fabric with an area of approximately 400 mm² were cut and placed on agar plates which had previously been innoculated with *Staphylococcus aureus*. The plates were then incubated at 35° C. for 24 hours.

After the 24 hour incubation, *Staphylococcus aureus* was not present in or on the fabric squares. Microscopic examination showed a halo or zone of inhibition around the singular threads.

EXAMPLE III

A standard water solution of the amine alkyl phosphate additive was prepared by dissolving 20 grams of the preferred amine alkyl phosphate additive from Example I in 980 ml. of water. The standard solution of the preferred amine alkyl phosphate additive was serially diluted down to 0.02% and was evaluated against representative Gram negative and Gram positive bacteria. One measured drop (0.05 ml) of the microbiocidal cleansing agent of the present invention was placed on previously inoculated agar plates (Nutrient Agar, Baltimore Biological Laboratory, Cockeysville, Md.) and incubated for 24 hours at 35° C. The area of inhibition was then measured and recorded. The results of the test are represented in Table A.

TABLE A

| Organisms | Vol. % | Area of Inhibition measured in mm |
|---|---|---|
| Staphylococcus aureus | 2.0 | 30 |
| Staphylococcus aureus | 1.0 | 20 |
| Staphylococcus aureus | 0.2 | 10 |
| Staphylococcus aureus | 0.02 | 0 |
| Pseudomonas aeruginosa | 2.0 | 10 |
| Pseudomonas aeruginosa | 1.0 | 10 |
| Pseudomonas aeruginosa | 0.5 | 10 |
| Pseudomonas aeruginosa | 0.02 | 0 |

As can be seen from the data in Table A, the microbiocidal cleansing agent of the present invention is an unexpectantly strong bactericide against both Gram positive and Gram negative organisms.

EXAMPLE IV

A dry free-flowing mixture comprising the microbiocidal cleansing agent of the present invention was prepared by mixing 0.3 grams of the amine alkyl phosphate additive from Example I with 138.5 grams of "All ®" detergent as purchased over the counter. One gram of the cleansing agent mixture was then placed in the center of appropriately innoculated petri dishes and incubated for 24 hours at 37° C. Control plates were also prepared with one gram samples of the detergent without any amine alkyl phosphate additive. After this period of incubation, each plate was examined and the diameters of the inhibition zones were measured. Control plates were also prepared with one gram samples of the detergent without any phosphate additive. The results are shown in Table B.

TABLE B

| Organism | Zone of Inhibition in mm for detergent and amine alkyl phosphate additive | Zone of Inhibition in mm for detergent |
|---|---|---|
| *Staphylococcus aureus* | 30 | 15 |
| *Pseudomonas aeruginosa* | 18 | 6 |

The detergent alone exhibited some microbiocidal activity because of the presence of sodium hypochlorite. However, the sodium hypochlorite would be washed out of fabrics during the rinsing process. In any event, the detergent plus additive demonstrated a significant increase in microbiocidal activity over the detergent alone.

While this invention has been described in detail with particular reference to preferred embodiments thereof, it will be understood that variations and modifications can be effected within the spirit and scope of the invention as described hereinbefore and as defined in the appended claims.

I claim:

1. A microbiocidal cleansing agent comprising:
    a mixture of a detergent and a microbiocidally effective amount of an amine alkyl phosphate additive having the following formula:

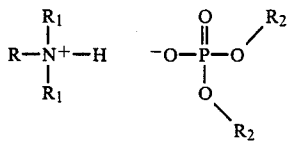

wherein
    R is an alkyl group containing from 1 to 24 carbon atoms;
    $R_1$ is an alkyl group containing from 1 to 3 carbon atoms; and
    $R_2$ is an alkyl group containing from 1 to 5 carbon atoms.

2. The microbiocidal cleansing agent of claim 1 wherein said amine alkyl phosphate additive has the following formula:

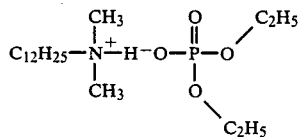

3. A microbiocidal cleansing agent comprising:
    a mixture containing water and a microbiocidally effective amount of an amine alkyl phosphate additive, said amine alkyl phosphate additive having the following formula:

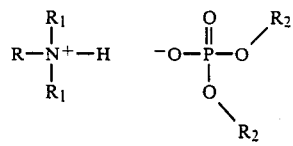

wherein
    R is an alkyl group containing from 1 to 24 carbon atoms;
    $R_1$ is an alkyl group containing from 1 to 3 carbon atoms; and
    $R_2$ is an alkyl group containing from 1 to 5 carbon atoms.

4. The microbiocidal cleansing agent of claim 3 wherein said amine alkyl phosphate additive has the following formula:

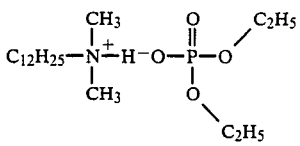

5. A method of preparing a microbiocidal cleansing agent comprising the steps of:
    (a) reacting phosphorus pentoxide with a hydroxy alkyl group of from 1 to 5 carbon atoms at a temperature between approximately 60° C. and 100° C. and allowing the reaction to proceed to completion;
    (b) reacting the reaction product of step (a) with a tertiary amine wherein said amine has one alkyl group of from 1 to 24 carbon atoms and two alkyl groups of from 1 to 3 carbon atoms; and
    (c) mixing a microbiocidally effective amount of the reaction product of Step (b) with a detergent.

6. The method of claim 5 wherein said tertiary amine is dodecyl bis(methyl)cocoamine.

7. A method of preparing a microbiocidal cleansing agent comprising the steps of:
    (a) reacting phosphorus pentoxide with a hydroxy alkyl group of from 1 to 5 carbon atoms at a temperature between approximately 60° C. and 100° C. and allowing the reaction to proceed to completion;
    (b) reacting the reaction product of step (a) with a tertiary amine wherein said amine has one alkyl group of from 1 to 24 carbon atoms and two alkyl groups of from 1 to 3 carbon atoms; and
    (c) mixing a microbiocidally effective amount of the reaction product of Step (b) with water.

8. The method of claim 7 wherein said tertiary amine is dodecyl bis(methyl)cocoamine.

* * * * *